United States Patent
Kim et al.

(10) Patent No.: US 12,364,973 B2
(45) Date of Patent: Jul. 22, 2025

(54) CATALYST FOR SELECTIVE HYDROGENATION OF ACETYLENE AND METHOD FOR PRODUCING SAME

(71) Applicant: KOREA RESEARCH INSTITUTE OF CHEMICAL TECHNOLOGY, Daejeon (KR)

(72) Inventors: Yong Tae Kim, Daejeon (KR); Sung Woo Lee, Daejeon (KR); Seung Ju Han, Daejeon (KR); Seok Ki Kim, Daejeon (KR); Hyun Woo Kim, Daejeon (KR); Jungho Shin, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 673 days.

(21) Appl. No.: 17/763,555

(22) PCT Filed: Sep. 3, 2020

(86) PCT No.: PCT/KR2020/011821
§ 371 (c)(1),
(2) Date: Mar. 24, 2022

(87) PCT Pub. No.: WO2021/071100
PCT Pub. Date: Apr. 15, 2021

(65) Prior Publication Data
US 2022/0339605 A1  Oct. 27, 2022

(30) Foreign Application Priority Data
Oct. 10, 2019 (KR) .................. 10-2019-0125473

(51) Int. Cl.
| | | |
|---|---|---|
| *B01J 23/44* | (2006.01) | |
| *B01J 21/08* | (2006.01) | |
| *B01J 35/61* | (2024.01) | |
| *B01J 37/02* | (2006.01) | |
| *B01J 37/08* | (2006.01) | |
| *C07C 5/09* | (2006.01) | |

(52) U.S. Cl.
CPC .............. *B01J 23/44* (2013.01); *B01J 21/08* (2013.01); *B01J 35/612* (2024.01); *B01J 37/0236* (2013.01); *B01J 37/08* (2013.01); *C07C 5/09* (2013.01); *C07C 2523/44* (2013.01)

(58) Field of Classification Search
CPC . B01J 23/44; B01J 35/612; B01J 21/08; B01J 37/0236; B01J 37/08; C07C 5/09; C07C 2523/44
USPC ......... 502/262, 339; 585/259, 260, 417–419, 585/434
See application file for complete search history.

(56) References Cited

U.S. PATENT DOCUMENTS

| | | |
|---|---|---|
| 4,387,258 A | 6/1983 | Vadekar et al. |
| 4,839,329 A | 6/1989 | Ihm et al. |

FOREIGN PATENT DOCUMENTS

| | | | | |
|---|---|---|---|---|
| EP | 0255877 A2 | * | 2/1988 | .......... C01B 33/107 |
| JP | 2017-18862 A | | 1/2017 | |
| JP | 2017018862 A | * | 1/2017 | .............. B01J 31/22 |
| KR | 10-2003-0041144 A | | 5/2003 | |
| KR | 10-2003-0061372 A | | 7/2003 | |
| KR | 10-2007-0116991 A | | 12/2007 | |
| KR | 20070116991 A | * | 12/2007 | .............. C07C 11/04 |
| KR | 10-2011-0112341 A | | 10/2011 | |
| KR | 20190133913 A | * | 12/2019 | .............. B01J 37/16 |

OTHER PUBLICATIONS

English translation of Written Opinion for PCT/KR2020/011821. (Year: 2020).*
International Search Report issued on Dec. 24, 2020, for corresponding International Application No. PCT/KR2020/011821.
Written Opinion issued on Dec. 24, 2020, for corresponding International Patent Application No. PCT/KR2020/011821.
Bond et al., "The Hydrogenation of Acetylenic Compounds and Diolefins," Catalysis by metals, Academic Press, New York, 1962, pp. 281-309.

* cited by examiner

*Primary Examiner* — Patricia L. Hailey
(74) *Attorney, Agent, or Firm* — Hauptman Ham, LLP

(57) ABSTRACT

The present invention relates to a catalyst for selective hydrogenation of acetylene and a preparation method thereof. More specifically, the catalyst and preparation method maximize the catalytic reaction rate at various reaction temperatures and suppress side reactions to minimize the generation of green oil and cokes and to improve the deactivation rate of a catalyst when preparing ethylene from acetylene. Thus, the catalyst and the preparation method provide a high conversion rate of acetylene and a high ethylene production yield.

7 Claims, No Drawings

CATALYST FOR SELECTIVE HYDROGENATION OF ACETYLENE AND METHOD FOR PRODUCING SAME

CROSS-REFERENCE TO RELATED APPLICATION

The present application is a national stage filing under 35 U.S.C § 371 of PCT application number PCT/KR2020/011821 filed on Sep. 3, 2020, which is based upon and claims the benefit of priorities to Korean Patent Application No. 10-2019-0125473, filed on Oct. 10, 2019, in the Korean Intellectual Property Office. All of the aforementioned applications are hereby incorporated by reference in their entireties.

TECHNICAL FIELD

The present invention relates to a catalyst for the selective hydrogenation of acetylene and to a method for preparing the same. More particularly, the present invention relates to a catalyst for selective hydrogenation of acetylene and to a preparation method thereof, the catalyst and method being useful for preparation of acetylene through selective hydrogenation.

BACKGROUND ART

Ethylene is a material used as a monomer in the production of various types of polymers and is produced by pyrolysis of naphtha or catalytic cracking of petroleum gas such as ethane, propane, or butane. Ethylene produced by one of the methods typically contains about 0.5 wt % to 2.0 wt % of acetylene. In order for such ethylene to be used as a monomer for production of a polymer, the concentration of acetylene needs to be to an appropriate level. This is because ethylene with a high acetylene content lowers the activity of a polymerization catalyst and deteriorates the physical properties of the produced polymer material. In the 1950s, the content of acetylene allowed in ethylene was reduced to 50 ppm. It was further reduced to 10 to 20 ppm in in the 1960s and have been recently yet further reduced to less than 2 ppm.

As a method of removing a trace amount of acetylene contained in ethylene, there are a solvent extraction method (refer to Patent Document 0001) and a catalyst-involved hydrogenation method. Nowadays, in the typical process, ethylene containing about 1% of acetylene and separated and discharged from the upper part of an ethylene separation tower is selectively hydrogenated using a hydrogenation catalyst to produce high-purity ethylene. This method incurs lower cost than the solvent extraction method.

As such a hydrogenation catalyst, various transition metals can be used. The most important consideration in the hydrogenation method is to selectively hydrogenate only acetylene without causing hydrogenation of ethylene. High selectivity results in high yield in production of ethylene.

In early years, at a low temperature, for example, below 300° C., sulfide catalysts such as nickel sulfide or nickel sulfide-tungsten or copper-based catalysts were used as selective acetylene hydrogenation catalysts. However, these catalysts have a problem in that the reactivity is low and the polymerization reaction is fast. This results in the catalyst pores being easily clogged, thereby shortening the regeneration cycle of the catalyst. When a noble metal is used as a catalyst, improved results can be obtained in reactivity and selectivity. In particular, it is known that the reactivity of palladium (Pd) is excellent in a low-temperature reaction (refer to Non-Patent Document 0001).

In order for the transition metal used for hydrogenation to act as an effective catalyst, the metal is required to have a large surface area. For this purpose, a method of dispersing a catalyst component using a support is used. Another reason for dispersing a catalyst component using a support is to facilitate removal of excessive reaction heat anticipated in a commercial process. When 1 mole of acetylene is hydrogenated to produce 1 mole of ethylene, more than 40 kcal of reaction heat is generated. In the case of an undispersed catalyst, the reaction heat is locally accumulated, making it difficult to control the temperature of a reactor. When the reaction temperature is raised, more acetylene is converted to ethylene, but the fraction of conversion from ethylene ethane also increases. Since the selectivity of the reaction changes depending on the reaction temperature, it is necessary to maintain an appropriate reaction temperature range and to control the reaction heat to fall within an appropriate range. In general, it is preferable to select a catalyst and reactor with which the temperature rise occurs within a range of 15° C. when acetylene is completely removed.

U.S. Pat. No. 4,387,258 discloses a catalyst manufacturing method in which a catalyst component is dispersed in a silica support, and U.S. Pat. No. 4,839,329 discloses a method of preparing a catalyst by dispersing palladium in a titanium dioxide support.

However, as in these related art documents, when a hydrogenation catalyst is prepared using a support and a acetylene conversion reaction is performed in various temperature ranges, there is a problem caused by a side reaction of the support. Since the supports used in the related art documents stated above exhibit high specific surface area and weak acidic properties, when the reaction proceeds at a relatively high temperature of 500° C. or higher, acetylene or ethylene is polymerized in the pores to produce green oil with 4 carbon atoms and cokes. The green oil and coke formed in this way block a part of the catalyst pores, thereby inhibiting reactants from having access to the catalyst pores. In addition, the green oil and coke avoid the active points of the hydrogenation reaction, thereby accelerating the deactivation of the catalyst. These problems result in shortening the regeneration cycle and lifespan of the catalyst.

Therefore, the inventors of the present invention have proceeded to develop an improved catalyst technology having a high selectivity even at a high reaction temperature of about 1,000° C. and inhibiting side reactions such as polymerization, thereby enabling efficient and stable production of ethylene from acetylene.

DOCUMENTS OF RELATED ART

Patent Document (Patent Document 0001) U.S. Pat. No. 4,387,258 (issued on Jun. 7, 1983)
(Patent Document 0002) U.S. Pat. No. 4,839,329 (Jun. 13, 1989)

Non-Patent Document (Non-Patent Document 0001) Bond et al., Catalysis by metals, Academic Press, New York, 281-309, 1962.

DISCLOSURE

Technical Problem

The main objective of the present invention is to solve the above-mentioned problems and is to provide a catalyst for selective hydrogenation of acetylene and a preparation method thereof, the catalyst and preparation method being capable of maximizing the catalytic reaction rate in various reaction temperature ranges and of suppressing side reactions to minimize the generation of green oil and coke and to improve the deactivation rate of the catalyst, thereby providing a high conversion rate from acetylene to ethylene and a high yield in production of ethylene.

Technical Solution

In order to achieve the above objective, an embodiment of the present invention provides a catalyst for selective hydrogenation of acetylene, the catalyst comprising: a catalyst support in a molten crystalline state containing silicon oxide; and palladium nanoparticles dispersed and supported on the catalyst support.

In a preferred embodiment of the present invention, the catalyst support may be cristobalite.

In a preferred embodiment of the present invention, the catalyst support may have a specific surface area of 1 m$^2$/g or less, and the amount of palladium that is supported may be 0.1 wt % to 50.0 wt %, with respect to the total weight of the catalyst.

Another embodiment of the present invention provides a method of manufacturing a catalyst for selective hydrogenation of acetylene, the method including: (a) melting and solidifying a silicon precursor to obtain a catalyst support in a molten crystalline state; (b) impregnating a palladium precursor into the catalyst support obtained in step (a); and (c) drying and heat-treating the impregnated support.

In another preferred embodiment of the present invention, the silicon precursor of step (a) may be one or more selected from the group consisting of quartz, silica, silicon, sodium silicate, amorphous aluminosilicate, alkoxysilane, SiN, SiAl, clay, and talc.

In another preferred embodiment of the present invention, the melting of step (a) may be performed in a temperature range of 1,500° C. to 3,000° C.

A further embodiment of the present invention provides a method of producing ethylene by hydrogenating acetylene in the presence of the catalyst for selective hydrogenation of acetylene.

In a further preferred embodiment of the present invention, the hydrogenation may be performed at a reaction temperature in a range of 100° C. to 1,000° C. and at a reaction pressure in a range of 0.01 bar to 5 bar.

Advantageous Effects

According to the present invention, when producing ethylene from acetylene, the catalyst reaction rate is maximized and side reactions are suppressed to minimize the generation of green oil and coke and to lower the deactivation rate of the catalyst, thereby providing a high conversion rate acetylene and a high yield in production of ethylene.

BEST MODE

Unless otherwise defined, all terms including technical and scientific terms used herein have the same meaning as commonly understood by those who are ordinarily skilled in the art to which this invention belongs. In general, the nomenclature used herein is well-known and commonly used in the art.

It will be further understood that the terms "comprises", "includes", or "has", when used in this specification, specify the presence of an element, but do not preclude the presence or addition of one or more other elements unless the context clearly indicates otherwise.

One aspect of the present invention relates to a catalyst for selective hydrogenation of acetylene, the catalyst comprising: a catalyst support in a molten crystalline state containing silicon oxide; and palladium nanoparticles dispersed and supported on the catalyst support.

In general, in the selective hydrogenation of acetylene, the hydrogenation reaction rate of ethylene is known to be 10 to 100 times faster than the hydrogenation reaction rate of acetylene (refer to Non-Patent Document 0001). When the hydrogenation of acetylene and the hydrogenation of ethylene compete, the hydrogenation of acetylene prevails because of the selective adsorption of acetylene to catalytic active sites. That is, the hydrogenation reaction of acetylene on the catalyst is mainly determined by the adsorption and desorption rates rather than the surface reaction rates.

In addition, when the acetylene hydrogenation reaction occurs at a reaction temperature of 500° C. or below, carbon deposition hardly occurs in all cases of the palladium catalyst. However, the reaction rate is relatively low and the reactants must be cooled. When the operation is performed at 500° C. or higher in the presence of the palladium catalyst, the reaction readily proceeds, but the hydrogenation of ethylene or the C—C bonding and dehydrogenation of acetylene are promoted. This, as a result, lowers the selectivity of ethylene and generates coke due to carbon. This affects the life of the catalyst. As the reaction temperature increases, more carbon deposition is generated.

Accordingly, the inventors of the present invention have made intensive efforts to develop a catalyst having high ethylene selectivity and superior coking resistance compared to conventional palladium catalysts in various reaction temperature ranges when selectively synthesizing ethylene from acetylene. As a result, the inventors have found that when palladium, which is a catalytically active component, was uniformly dispersed as nanoparticles on a catalyst support that is in a molten crystalline state containing silicon oxide and thus has a Si—O—Pd bond with the catalyst support, coke generation due to carbon on the palladium surface was suppressed, and the concentration in a specific distance between catalytic active sites was reduced. This inhibited adsorption of ethylene and intermediate products, and thus it was possible to selectively manufacture ethylene from acetylene without side reaction such as hydrogenation and additional C—C bonding reaction. Thus, the present invention has completed.

More specifically, the catalyst for selective hydrogenation of acetylene, according to the present invention, has a form in which palladium, which is a catalytically active component, is impregnated into silicon oxide in a crystalline molten state. Palladium nanoparticles are selectively embedded in the surface of silicon oxide. A silicon precursor is melted and solidified so that the palladium precursor can be impregnated into the surface of the catalyst support that is in a molten crystalline state.

In this case, the catalyst support in the molten crystalline state may be preferably cristobalite obtained by melting and solidifying a silicon precursor. The cristobalite has a small surface area due to its large crystal size, is low in the concentration of surface defects, and has low acidity. When the cristobalite is used as a catalyst support in a catalyst for the selective hydrogenation of acetylene, it has the effects of suppressing the strong adsorption of acetylene to the surface and pores of the support and inhibiting unnecessary C—C bonding and the dehydrogenation of the adsorbed acetylene.

In addition, the catalyst support may have a specific surface area of 1 m$^2$/g or less, preferably 0.0001 m$^2$/g to 0.5 m$^2$/g. In addition, the amount of palladium supported may be 0.1 wt % to 50.0 wt %, preferably 0.3 wt % to 10.0 wt %, relative to the total weight of the catalyst. With respect to 100 wt % of the supported palladium, the reducible palladium may be 4,700 μmol Pd/cm$^2$ or less, and preferably 1,000 μmol Pd/cm$^2$ or less.

When the specific surface area of the catalyst support exceeds 1 m$^2$/g, the proximity of the reaction sites in the catalyst surface increases, resulting in surface re-adsorption of the intermediate product. In addition, mass transfer between the reactant and the intermediate product in the pores is limited, resulting in occurrence of side reactions. For those reasons, carbon deposition occurs.

In addition, when the supported amount of palladium is less than 0.1 wt % relative to the total weight of the catalyst, the amount of palladium that can act as a dopant is small and the reaction efficiency is decreased. When the supported amount exceeds 50 wt %, the amount of palladium serving as reaction active sites in the surface of the catalyst is large, and the size of palladium particles increases. Thus, the growth rate of the hydrocarbons of the coke and the intermediate product increases.

On the other hand, when the amount of reducible palladium exceeds 4,700 μmol Pd/cm$^2$ with respect to 100 wt % of the supported palladium, the proximity of the reaction active sites in the catalyst surface increases, resulting additional hydrogenation and side reactions such as dehydrogenation, oligomerization, and cyclization due to surface re-adsorption of intermediate products. This may lower the selectivity of ethylene, resulting in carbon deposition.

Another aspect of the present invention relates to a method of manufacturing a catalyst for selective hydrogenation of acetylene, the method including: (a) melting and solidifying a silicon precursor, thereby obtaining a catalyst support in a molten crystalline state; (b) impregnating a palladium precursor into the catalyst support obtained in step (a) through incipient impregnation; and (c) drying and heat-treating the impregnated support.

In the method of preparing a catalyst for selective hydrogenation of acetylene, according to the present invention, first, a silicon precursor is melted and solidified to obtain a catalyst support in a molten crystalline state [step (a)].

The silicon precursor may be a solid material containing silicon. Preferably, the silicon precursor may be one or more selected from the group consisting of quartz, silica, silicon, sodium silicate, amorphous aluminosilicate, alkoxysilane, SiN, SiAl, clay, and talc. More preferably, the silicon precursor may be quartz.

When the silicon precursor is impregnated with elemental palladium, the melting and solidification steps are performed to release —OH groups and to control the surface area and the density of surface defects of the catalyst support. The melting may be performed at a temperature at which the silicon precursor can be melted in an air atmosphere. For example, the melting may be performed at 1,500° C. to 3,000° C. for 1 hour to 10 hours. When the temperature in the melting step is lower than 1,500° C., it is difficult to control the surface area of the catalyst support because the melting of the silicon precursor is not preferably performed. When the temperature exceeds 3,000° C., the component of the catalyst support may be vaporized, resulting in a loss. Therefore, it is difficult to obtain a uniform catalyst.

The molten melt is solidified to obtain a catalyst support in a molten crystalline state. The solidification may be performed by rapid cooling or natural cooling. The rapid cooling may be performed by gas cooling, water cooling, oil cooling, liquid nitrogen cooling, etc. Preferably, the rapid cooling may be performed at a rate in the range of 1° C./min to 100° C./min.

The gas used in the gas cooling may be at least one selected from the group consisting of inert gas and air. The oil used in oil cooling may be mineral oil, rapeseed oil, silicone oil, or the like.

In addition, the catalyst support according to the present invention can control the surface area of the catalyst support by repeating the melting and solidifying steps described above. The melting and solidification steps may be repeated one or more times, and preferably 2 to 5 times.

The crystal structure of the catalyst support prepared through the above preparation method is α-crystobalite, and the structure is reversibly converted into β-crystobalite when heated at 200° C. to 300° C.

Thereafter, the obtained catalyst support is impregnated with a palladium precursor [step (b)].

Any impregnation method can be used without limitation method for the impregnation step. Preferably, the impregnation method may be incipient impregnation and may be performed at a temperature in the range of from room temperature to 80° C. for 0.1 to 10 hours. In the impregnation step, the palladium precursor may be mixed in an amount of 0.1 wt % to 50 wt % respect to the total weight of the catalyst. When the palladium precursor is mixed in an amount of less than 0.1 wt %, the catalyst activity drops sharply. On the other hand, when the amount of the palladium precursor exceeds 50 wt %, the reactivity of the palladium is rather lowered due to the lowering the dispersibility of the active material in the catalyst support.

In addition, examples of the palladium precursor include palladium nitride such as Pd(NO$_3$)$_2$, palladium sulfide such as PdSO$_4$, palladium chloride such as PdCl$_2$, palladium oxides such as Pd(OAc)$_2$, Pd(C$_5$H$_7$O$_2$)$_2$, and Pd(C$_2$H$_5$CO$_2$)$_2$ but are not limited thereto.

Thereafter, the impregnated material is dried and then heat treated to prepare a catalyst for selective hydrogenation of acetylene [step (c)].

The drying is to remove impurities such as a solvent contained in the impregnated material and to facilitate calcination to be described later. The conditions for the drying are not particularly limited if it is possible to remove the solvent. Preferably, the drying may be performed at 80° C. to 120° C. for 0.5 to 36 hours.

On the other hand, the dried product is heated in air, oxygen, or inert atmosphere to 300° C. to 1,000° C. at a temperature increase rate of 1° C./min or more, and preferably 2° C./min to 1,000° C./min. When the heat treatment temperature is lower than 300° C., it is not easy to remove impurities remaining in the dried material and to obtain a uniform catalyst whereas when the temperature exceeds 1,000° C., agglomeration may occur and the catalytically active component vaporizes, resulting in a loss of the component. In this case, the heat treatment time is determined to ensure sufficient calcination, and it is preferably 0.1 to 10 hours.

The catalyst for selective hydrogenation of acetylene prepared in this way may be uniformly mixed with an inorganic binder, an organic binder, water, etc. to obtain a catalyst mixture. This catalyst mixture is molded to prepare a catalyst molded body.

The organic binder may be a material that is commonly used in the related art, and is not particularly limited. Preferably, the organic binder is at least one selected from methyl cellulose, ethylene glycol, polyol, food oil, and organic fatty acid. Specifically, it is preferable to use hydroxy methyl cellulose or polyvinyl alcohol as the organic binder. In addition, the inorganic binder may be a material commonly used in the art, and is not particularly limited. It is preferable to use at least one selected from solid silica, solid alumina, solid silica-alumina, silica sol, alumina sol, and water glass as the inorganic binder. Specifically, it is preferable to use fumed silica, silica solution, boehmite, or an alumina solution as the inorganic binder.

The catalyst mixture is typically prepared as a catalyst molded body by coating the catalyst mixture on a catalyst structure such as a honeycomb structure or a monolith structure, or by directly extruding the catalyst mixture. In addition, the catalyst mixture may be used by being directly coated on the inner wall surface of a reactor. In this case, the coating and extrusion molding of the catalyst mixture can be easily performed by methods used in the art, and thus detailed descriptions will be omitted.

A further aspect of the present invention relates to a method of producing ethylene by hydrogenating acetylene in the presence of the catalyst for selective hydrogenation of acetylene.

The ethylene production method according to the present invention can selectively produce ethylene by using acetylene as a raw material in the presence of the catalyst for selective hydrogenation of acetylene described above.

The hydrogenation reaction may be carried out at a reaction temperature in the range of 100° C. to 1,000° C. and at a reaction pressure in the range of 0.01 bar to 5 bar. Preferably, the hydrogenation reaction may be carried out at a temperature in the range of 500° C. to 1,000° C. and a reaction pressure in the range of 0.01 bar to 5 bar.

When the reaction temperature of the hydrogenation reaction is lower than 100° C., the reaction efficiency is low so that the selectivity to ethylene is reduced. When the reaction temperature exceeds 1,000° C., the carbon deposition rate increases, the life of the catalyst is shortened, and the side reaction of the intermediate product, such as hydrogenation, dehydrogenation, oligomerization, cyclization, cracking, etc. may occur.

In addition, when the reaction pressure of the hydrogenation reaction is lower than 0.01 bar, the reactants and products are easily carbonized, thereby causing a problem in catalyst stability. On the other hand, when the reaction pressure exceeds 5 bar, the carbon chain growth rate of the reactants and intermediate products increases, thereby causing a problem in catalyst stability, and the process operation becomes complicated in terms of safety issues. Therefore, the reaction pressure exceeding 5 bar is not preferable.

On the other hand, for the hydrogenation of acetylene using the catalyst of the present invention, either a fixed bed reactor or a fluidized bed reactor may be used, and the reaction may be carried out in any phase of gaseous, liquid, or mixed phase. As an example of a gas phase reaction, when hydrogen gas and a mixture containing acetylene as a reactant are introduced into the reactor through the inlet of the reactor in which the catalyst of the present invention is charged, the acetylene is hydrogenated in the reactor and the reaction product is discharged through the outlet of the reactor. In this case, the mixture containing acetylene may include methane, ethane, ethylene, benzene, naphthalene, etc. in addition to acetylene, and the molar ratio of hydrogen to acetylene may be 0.5 to 50.

When the molar ratio of hydrogen to acetylene is less than 0.5, the C—C bonding reaction of acetylene is faster than the hydrogenation of acetylene at a reaction temperature of 500° C. or higher, so that an aromatic compound such as benzene can be produced. This aromatic compound may combine with acetylene to produce coke. When the molar ratio of hydrogen to acetylene exceeds 50, ethane may be formed due to hydrogenation of the produced ethylene.

The ethylene preparation method according to the present invention uses a catalyst that suppresses the coke generation caused by carbon on the palladium surface and reduces the concentration in the specific distance of the catalytic reaction active sites, thereby suppressing the re-adsorption of ethylene and the intermediate products. That is, with the use of the catalyst, it is possible to minimize the generation of green oil and cokes by maximizing the catalytic reaction rate and suppressing side reactions, and to provide a high conversion rate of acetylene and a high yield in production of ethylene.

The present invention will be described in more detail with reference to examples described below. The examples described below are presented only to help understanding of the present invention, and the scope of the present invention is not limited thereto.

Example 1

As a silicon precursor, quartz was melted at 1,700° C. for 2 hours, and then rapidly cooled by water cooling to obtain cristobalite (CRS). Next, 0.075 g of $Pd(NO_3)_2.2H_2O$ was mixed well with 5 mL of ethanol, and the mixture was supported on 6 g of the cristobalite (CRS) at room temperature for 1 hour through incipient wetness impregnation. The Pd-supported CRS was dried at 110° C. for 3 hours, then heated to 400° C. at a rate of 2° C./min, then heat-treated in an oxygen atmosphere for 4 hours, and heated again to 850° C. at a rate of 6° C./min. Next, the product was heat-treated in a reducing atmosphere with 50% $H_2$/He for 1 hour, and thus a Pd/CRS catalyst having a palladium loading of 0.5 wt % relative to the total weight of the catalyst was obtained. The Pd/CRS catalyst had a specific surface area of 0.5 $m^2$/g or less which was measured by Micromeritics ASAP 2420.

Comparative Example 1

As in Example 1, 0.075 g of $Pd(NO_3)_2.2H_2O$ was mixed well with 5 mL of ethanol, and the mixture was supported on 6 g of the cristobalite (CRS). The Pd-supported CRS was dried at 110° C. for 3 hours, then heated to 1,700° C. at a rate of 10° C. per minute, and then melted in an oxygen atmosphere for 6 hours. Thus, a Pd—CRS catalyst containing 0.5 wt % of palladium with respect to the total weight of the catalyst was obtained. Next, the Pd—CRS catalyst was heated to 850° C. at a rate of 6° C. per minute and then heat-treated in a reducing atmosphere with 50% $H_2$/He for 1 hour, thereby producing a catalyst having a specific surface area 0.5 $m^2$/g or less measured with Micromeritics ASAP 2420.

Comparative Examples 2 to 4

Gamma-alumina was used as a support. 0.075 g of $Pd(NO_3)_2.2H_2O$ was mixed well with 5 mL of ethanol, and the mixture was supported on $Al_2O_3$ through incipient wetness impregnation. The Pd-supported $Al_2O_3$ was dried at 110° C. for 3 hours, then heated to 400° C. at a rate of 2° C. per minute, and then fired in an oxygen atmosphere for 4 hours. Thus, a catalyst containing 0.5 wt % of palladium with respect to the total weight thereof was obtained. Catalysts were prepared in the same manner as described above, but the support (i.e., support) was changed to $CeO_2$ and $TiO_2$ in Comparative Examples 3 and 4, respectively.

Comparative Examples 5 to 32

Catalysts were prepared in the same manner as in Example 1, but catalysts containing 0.5 wt % metal were obtained using metal precursors and supports shown in Table 1. Here, all metal precursors containing nitrate ($NO_3$) were used as the metal precursor, except for $Pt(NH_3)_4(NO_3)_2$, $Ru(NO)(NO_3)_x$, $IrCl_3$, $H_3BO_3$, $NH_4VO_3$, $(NH_4)_6Mo_7O_{24}$, $C_{15}H_{21}O_6Rh$, $HAuCl_4$, $H_3PO_4$, $HReO_4$, $(NH_4)_{10}(H_2W_{12}O_{42})$.

Experimental Example 1: Hydrogenation of Acetylene

Using the catalysts prepared in Examples and Comparative Examples, the hydrogenation reaction of acetylene was carried out for 10.2 hours to evaluate catalyst performance. The reactor used in the test was a fixed bed reactor. A quartz tubular reactor with an inner diameter of 7 mm was installed in the furnace having a heating zone with a total height of 150 mm. The prepared catalyst was pulverized to have a particle size of 425 to 850 µm and the catalyst particles were charged into the quartz tube reactor. Next, the reactant containing acetylene under the reaction conditions was supplied at a flow rate of 80 mL/min at 850° C. by a mass flow controller. The reactant is composed of 0.25% $C_2H_2$, 12.5% $H_2$, 86.25% He, and 1.0% Ar. Ar gas was used according to an internal standard.

The gaseous hydrocarbon of the obtained products were analyzed by gas chromatography (GC) using Series 6500 manufactured by YL Instrument Co., Ltd., and the gaseous products were analyzed with a thermal conductivity detector (TCD) connected to a ShinCarbon ST column, and two flame ionization (FID) detectors to which Rt-alumina BOND and RTx-VMS columns are connected. $C_2H_2$, $CH_4$ and Ar were separated by the ShinCarbon ST column and detected by TCD, and the conversion rate was calculated using the area of acetylene compared to the area of Ar in compliance with an internal standard. Light hydrocarbons in the range of C1 to C5 and benzene were separated by the Rt-alumina BOND column and detected by the FID, and aromatic compounds including benzene were separated by the RTx-VMS column and detected by the FID. Through detection of unreacted gases and detection of products, the carbon balance was maintained at 98% or more. All gases were quantified using standard samples. The coke selectivity was calculated the equation "Scoke=100−Σ product selectivity". The reaction rate for a total reaction time of 10.2 hours was calculated on the basis of the supported metal catalyst, and the calculated acetylene conversion rate and the product selectivity. Ethylene selectivity in the resulting hydrocarbons (methane, ethane, C3, C4, C5, benzene, toluene, naphthalene, and alkyl-aromatics) was calculated. In addition, the deactivation constant was calculated on the basis of the decrease in the conversion rate according to the reaction time. The calculation results are shown in Table 1. Table 1 shows the results measured in the way described above.

TABLE 1

| Classification | Catalyst component | Acetylene consumption rate (mmolC gcat$^{-1}$h$^{-1}$) | Hydrocarbon production rate (mmolC gcat$^{-1}$h$^{-1}$) | Cokes production rate (mmolC gcat$^{-1}$h$^{-1}$) | Selectivity (%) Ethane | Selectivity (%) Ethylene | Deactivation rate constant (kd) |
|---|---|---|---|---|---|---|---|
| Example 1 | Pd/CRS | 3100.8 | 2990.6 | 110.3 | 7.2 | 78.4 | 0 |
| Comparative Example 1 | Pd-CRS | 4647.5 | 4290.1 | 357.4 | 4.4 | 85.6 | 0.057 |
| Comparative Example 2 | Pd/Al$_2$O$_3$ | 9765.3 | 7796.9 | 1968.4 | 23.1 | 58.4 | 0.037 |
| Comparative Example 3 | Pd/CeO$_2$ | 2429.3 | 2082.7 | 346.6 | 3.0 | 80.7 | 0.294 |
| Comparative Example 4 | Pd/TiO$_2$ | 2806.4 | 2606.6 | 199.7 | 3.2 | 81.6 | 0.229 |
| Comparative Example 5 | Co/CRS | 802.8 | 576.6 | 250.9 | 2.3 | 72.8 | 0.035 |
| Comparative Example 6 | Mg/CRS | 563.7 | 558.1 | 7.2 | 1.8 | 76.0 | 0.064 |
| Comparative Example 7 | K/CRS | 919.1 | 884.5 | 34.6 | 1.8 | 76.9 | 0.059 |
| Comparative Example 8 | Li/CRS | 531.0 | 531.0 | 0 | 1.9 | 78.4 | 0.118 |
| Comparative Example 9 | Ni/CRS | 701.4 | 644.7 | 56.7 | 2.3 | 72.5 | 0.082 |
| Comparative Example 10 | Na/CRS | 532.4 | 532.4 | 0 | 1.7 | 77.0 | 0.035 |
| Comparative Example 11 | Cu/CRS | 556.6 | 556.6 | 0 | 1.9 | 77.6 | 0.184 |
| Comparative Example 12 | Cr/CRS | 536.4 | 536.4 | 0 | 1.8 | 78.0 | 0.065 |
| Comparative Example 13 | Zn/CRS | 580.4 | 580.4 | 0 | 1.9 | 78.1 | 0 |
| Comparative Example 14 | Pt/CRS | 1746.3 | 1621.3 | 125.1 | 7.9 | 83.7 | 0.158 |
| Comparative Example 15 | Ga/CRS | 928.2 | 511.9 | 416.4 | 1.7 | 75.6 | 0.218 |
| Comparative Example 16 | W/CRS | 532.6 | 527.5 | 5.1 | 1.8 | 77.9 | 0.124 |
| Comparative Example 17 | Gd/CRS | 532.5 | 522.7 | 9.8 | 1.7 | 77.4 | 0.136 |

TABLE 1-continued

| Classification | Catalyst component | Acetylene consumption rate (mmolC gcat$^{-1}$h$^{-1}$) | Hydrocarbon production rate (mmolC gcat$^{-1}$h$^{-1}$) | Cokes production rate (mmolC gcat$^{-1}$h$^{-1}$) | Selectivity (%) Ethane | Selectivity (%) Ethylene | Deactivation rate constant (kd) |
|---|---|---|---|---|---|---|---|
| Comparative Example 18 | Rh/CRS | 1291.5 | 1204.0 | 87.6 | 3.5 | 85.0 | 0.022 |
| Comparative Example 19 | Mo/CRS | 449.2 | 445.3 | 3.8 | 1.5 | 74.9 | 0.071 |
| Comparative Example 20 | Ir/CRS | 542.4 | 542.4 | 0 | 1.8 | 77.9 | 0.037 |
| Comparative Example 21 | Au/CRS | 514.9 | 474.3 | 40.6 | 1.5 | 76.0 | 0.127 |
| Comparative Example 22 | In/CRS | 631.9 | 491.0 | 140.9 | 1.4 | 76.4 | 0.191 |
| Comparative Example 23 | Ag/CRS | 587.6 | 582.0 | 5.6 | 1.9 | 79.1 | 0.027 |
| Comparative Example 24 | Al/CRS | 1304.9 | 1248.8 | 56.1 | 3.6 | 85.4 | 0.105 |
| Comparative Example 25 | Ca/CRS | 518.9 | 518.9 | 0 | 1.6 | 75.5 | 0.020 |
| Comparative Example 26 | La/CRS | 458.3 | 481.2 | 4.1 | 1.4 | 75.1 | 0.054 |
| Comparative Example 27 | Zr/CRS | 467.4 | 447.1 | 20.2 | 1.4 | 74.4 | 0.022 |
| Comparative Example 28 | Ce/CRS | 529.0 | 529.0 | 0 | 1.7 | 75.3 | 0.051 |
| Comparative Example 29 | V/CRS | 436.0 | 420.4 | 15.6 | 1.2 | 72.9 | 0.006 |
| Comparative Example 30 | B/CRS | 461.8 | 461.4 | 0.5 | 1.6 | 74.9 | 0.046 |
| Comparative Example 31 | P/CRS | 537.7 | 476.2 | 61.6 | 2.5 | 77.7 | 0.010 |
| Comparative Example 32 | Cr/CRS | 470.5 | 470.5 | 0 | 1.5 | 77.4 | 0.019 |

As shown in Table 1, in Example 1, although the hydrocarbon production rate was 30% lower than that of Comparative Example 1, the coke production rate was reduced by 70% or more. In addition, the deactivation occurred in Comparative Example 1 but the deactivation did not occur for 10.2 hours in Example 1. Though the test, it was confirmed that the catalyst prepared in Example 1 selectively generate ethane and ethylene while not generating cokes at a high temperature of 850° C. In addition, as in Comparative Examples 2 to 4, it was confirmed that the deactivation rate constant was high when the Pd catalyst was prepared using different types of supports and then the reaction was performed. In particular, the catalyst prepared in Example 1 was 3.1 times lower in the acetylene consumption rate than that of the Pd catalyst of Comparative Example 2 in which alumina was used as the support and was also 17.8 times lower in the coke production rate. That is, the catalyst prepared in Example 1 selectively hydrogenated acetylene while resisting coke. In addition, in the case of the catalysts of Comparative Examples 5 to 32, it was confirmed that the catalyst of Example 1 selectively hydrogenated acetylene while having superior resistance to coke at 850° C. compared to the catalysts of Comparative Examples 5 to 32.

Therefore, the catalyst for the selective hydrogenation of acetylene, according to the present invention, maximizes the catalytic reaction rate and minimizes coke generation in the production of ethylene, and provides a high conversion rate of acetylene and a high yield in production of ethylene and aromatic compounds.

Although the present invention has been described with reference to the embodiments, other embodiments may be configured within the spirit and scope of the present invention. Accordingly, the scope of the present invention is defined only by the appended claims and their equivalents, and is not limited by the specific embodiments described herein.

The invention claimed is:

1. A catalyst for selective hydrogenation of acetylene, the catalyst comprising: a catalyst support in a molten crystalline state containing silicon oxide; and palladium nanoparticles dispersed and supported on the catalyst support,
    wherein a reducible portion of the palladium nanoparticles is 4,700 μmol Pd/cm$^2$ or less with respect to 100 wt % of the palladium nanoparticles.

2. The catalyst according to claim 1, wherein the catalyst support is cristobalite.

3. The catalyst according to claim 1, wherein the catalyst is configured such that the catalyst support has a specific surface area of 1 m$^2$/g or less and the palladium nanoparticles are supported in an amount of 0.1 to 50.0 wt % with respect to the total weight of the catalyst.

4. A method of preparing a catalyst for selective hydrogenation of acetylene, the method comprising:
    melting and solidifying a silicon precursor, thereby obtaining a catalyst support in a molten crystalline state;
    impregnating a palladium precursor into the catalyst support obtained; and
    drying and heat-treating the impregnated support,
    wherein the melting is performed at a temperature in a range of 1,500° C. to 3,000° C.

5. The method of claim 4, wherein the silicon precursor comprises one or more selected from the group consisting of quartz, silica, silicon, sodium silicate, amorphous aluminosilicate, alkoxysilane, SiN, SiAl, clay, and talc.

6. A method of preparing ethylene by hydrogenating acetylene in the presence of the catalyst of claim 1.

7. The method of claim 6, wherein the hydrogenation reaction is performed at a reaction temperature in a range of 100° C.~1,000° C. and at a reaction pressure in a range of 0.01 bar~5 bar.

* * * * *